(12) United States Patent
Prigent et al.

(10) Patent No.: US 7,514,231 B2
(45) Date of Patent: Apr. 7, 2009

(54) ANTI-AURORA-A MONOCLONAL ANTIBODY, METHOD FOR OBTAINING SAME AND USES THEREOF FOR DIAGNOSING AND TREATING CANCERS

(75) Inventors: Claude Prigent, Thorigne-Fouilard (FR); Anne Martin, Rennes (FR)

(73) Assignees: Centre National de la Recherche Scientifique, Paris Cedex (FR); Etablissement Francais du Sang-Bretagne, Rennes Cedex (FR)

( * ) Notice: Subject to any disclaimer, the term of this patent is extended or adjusted under 35 U.S.C. 154(b) by 322 days.

(21) Appl. No.: 10/517,645

(22) PCT Filed: Jun. 12, 2003

(86) PCT No.: PCT/FR03/01772

§ 371 (c)(1), (2), (4) Date: Feb. 10, 2005

(87) PCT Pub. No.: WO03/106500

PCT Pub. Date: Dec. 24, 2003

(65) Prior Publication Data

US 2007/0117163 A1 May 24, 2007

(30) Foreign Application Priority Data

Jun. 12, 2002 (FR) .................................. 02 07212

(51) Int. Cl.
*C07K 16/40* (2006.01)
*G01N 33/574* (2006.01)

(52) U.S. Cl. .................................. 435/7.23; 530/388.26

(58) Field of Classification Search ................ 435/7.23; 530/388.26

See application file for complete search history.

(56) References Cited

U.S. PATENT DOCUMENTS 5,962,312 A  10/1999  Plowman et al.

FOREIGN PATENT DOCUMENTS

WO  WO 97/22702  6/1997

OTHER PUBLICATIONS (Sun et al., Biochem Biophys Res Commun. Jan. 5, 2007;352(1):220-5).*
Fundamental Immunology 242 (William E. Paul, M.D. ed., 3d ed. 1993), p. 1.*
HyCult Biotechnology datasheet for 35C1 (p. 1, Feb. 2004).*
Honda et al. (Oncogene 19:2812-2819 (2000).*
Giet et al. (J. Cell Sci. 114: 2095-2104 (2001).*
Shindo et al. (Biochem. Biophys. Res. Comm. 244:285-292 (1998).*
Bischoff et al. (Trends Cell Biol. 9:454-459 (1999).*
Arlot-Bonnemains et al., "Identification of a Functional Destruction Box in the *Xenopus laevis* Aurora-A Kinase pEg2," FEBS Letters 508:149-152, 2001.
Cremet et al., "Preparation and Characterization of a Human Aurora-A Kinase Monoclonal Antibody," Molecular and Cellular Biochemistry 243:123-131, 2003.
Tanaka et al., "Centrosomal Kinase AIK1 is Overexpressed in Invasive Ductal Carcinoma of the Breast," Cancer Research 59:2041-2044, 1999.

* cited by examiner

*Primary Examiner*—David J. Blanchard
*Assistant Examiner*—Lynn Bristol
(74) *Attorney, Agent, or Firm*—Clark & Elbing LLP

(57) ABSTRACT

The invention concerns a monoclonal antibody directed against mammalian aurora-A kinase, the method for obtaining same, as we ll as its uses in cancer diagnosis and prognosis, and in pharmaceutical compositions for cancer treatment.

12 Claims, 6 Drawing Sheets

Human aurora-A

MCF7 cells

Aurora-A (green)
γ-tubulin (red)
DNA (blue)

Murine aurora-A

LLC1 cells

ANTI-AURORA-A MONOCLONAL ANTIBODY, METHOD FOR OBTAINING SAME AND USES THEREOF FOR DIAGNOSING AND TREATING CANCERS

CROSS-REFERENCE TO RELATED APPLICATIONS

This application is a U.S. national stage application under 35 U.S.C. § 371 of PCT/FR03/01772, filed Jun. 12, 2003, which claims priority from French application number 02/07212, filed Jun. 12, 2002, the contents of each of which are incorporated herein by reference.

STATEMENT REGARDING FEDERALLY SPONSERED RESEARCH OR DEVELOPMENT

Not Applicable

THE NAMES OF PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

A subject of the present invention is a monoclonal antibody directed against aurora-A kinase of mammals, method for its obtention, as well as its uses in the context of the diagnosis or prognosis of cancers, and in pharmaceutical compositions for the treatment of cancers.

The aurora-A protein kinase is an oncogene, its overexpression in Rat-1 cells is sufficient to cause the appearance of a transformed phenotype and the implantation of these transformed cells into immunodeficient mice causes tumours to appear. (Bischoff et al., 1998; Zhou et al., 1998). The gene coding for this kinase is localized on the chromosome 20 at 20q13, amplicon frequently detected in numerous tumours (breast, colon, stomach cancers).

The overexpression of the aurora-A protein kinase has been observed in numerous tumours. Interestingly, the presence of this kinase in an abnormal quantity is not correlated to a proliferation detected by staining with a specific proliferation marker such as PCNA. Aurora-A is therefore a specific marker of the tumoral aspect of the cells (Tanaka et al., 1999; Takahashi et al., 2000).

Aurora-A belongs to a multigenic family of protein kinases called aurora, it comprises three members: aurora-A (described previously) aurora-B (Prigent et al., 1999) and aurora-C (Bernard et al., 1998). Although only aurora-A has a real oncogenic power the two other kinases have also been found overexpressed in the same tumours (Giet and Prigent, 1999).

The amplification of the gene coding for aurora-A is associated with the presence of an abnormally high activity of the protein kinase in these tumours. Moreover the ectopic overexpression of this kinase in cells in culture is sufficient to cause a transformed phenotype to appear, these cells transplanted into immunodeficient mice cause tumours to appear.

The overexpression of aurora-A kinase is very closely linked to the cancerous state of a cell. This overexpression of aurora-A kinase induces a polyploidy of the cells and causes an amplification of the centrosomes, two events which precede a poor prognosis for breast cancer for example.

It is therefore important to be able to precisely measure the expression of this kinase in cancerous pathologies, both at the level of the mRNA and the protein.

Now, the measurement of the expression of the aurora-A protein kinase depends entirely on the use of a good monoclonal antibody.

However, no sufficiently specific monoclonal antibody directed against the aurora-A protein kinase was able to be obtained until now, or is available commercially.

BRIEF SUMMARY OF THE INVENTION

The subject of the present invention is to provide a reliable anti-aurora-A monoclonal antibody, which links with this protein with a sufficient specificity and sensitivity in order to envisage its use for purposes of experimental research, as well as in the field of diagnosis, prognosis and treatment of cancers.

The invention relates to an anti-aurora-A monoclonal antibody specifically recognizing the human and murine aurora-A kinase, and having the following properties:

it can be fixed on the membranes containing the human or murine aurora-A protein, it allows detection, and, if appropriate, purification, of the human and murine aurora-A protein by immunoprecipitation, it allows the staining of biological tissues where the aurora-A protein is secreted and, it does not inhibit the enzymatic activity of the human and murine aurora-A protein, said monoclonal antibody being as obtained by:

five injections spread over fifteen days to mice of recombinant aurora-A protein kinase produced by *E. coli* bacteria transformed with a bacterial expression vector in the genome of which the human cDNA coding for aurora-A has been inserted, sacrificing said mice, and fusion between cells from the spleen of these mice and hamster cells immortalized in culture in order to obtain hybridomas, screening of the hybridomas producing an antibody capable of immunoprecipitating the recombinant protein used for the immunization of the mice during the preceding stage, and recovery of the positive hybridomas after this first screening, screening of the hybridomas recovered in the preceding stage, producing an antibody capable of immunoprecipitating the endogenous aurora-A protein from an extract of human HeLa cells in culture, and recovery of the positive hybridomas after this second screening, screening of the hybridomas recovered in the preceding stage, producing an antibody capable of recognizing in indirect immunofluorescence the centrosomes and the poles of the mitotic spindle of human cells in culture, and recovery of the positive hybridomas after this third screening, screening of the hybridomas recovered in the preceding stage, producing an antibody capable of immunoprecipitating the endogenous aurora-A protein of mice from an extract of murine cells in culture, and recovery of the positive hybridomas after this fourth screening, screening of the hybridomas recovered in the preceding stage, producing an antibody capable of recognizing in indirect immunofluorescence the centrosomes and the poles of the mitotic spindle of murine cells in culture, recovery and purification by cloning a positive hybridoma after the previous screening stage, and producing a monoclonal antibody possessing all of the properties defined above.

Therefore, a subject of the invention is more particularly a monoclonal antibody as defined above, also called 35C1 antibody, said antibody being secreted by the hybridoma deposited on the 12th Jun. 2003 at the Collection Nationale de Cultures de Microorganismes (CNCM) of the Institut Pasteur under the number I-3050.

A subject of the invention is also the use of a monoclonal antibody as defined above, and more particularly of the above-mentioned 35C1 antibody, for the implementation of an in vitro diagnostic or prognostic method for cancers in humans or animals.

A subject of the invention is more particularly the use of a monoclonal antibody as defined above, and more particularly the above-mentioned 35C1 antibody, for the implementation of an in vitro diagnostic or prognostic method for solid tumours, such as breast cancers, stomach cancers and colorectal cancers.

The invention also relates to the above-mentioned use of a monoclonal antibody as defined above, and more particularly of the above-mentioned 35C1 antibody, in combination with a cell proliferation marker, such as a marker of the PCNA protein (Tanaka et al., 1999; Takahashi et al., 2000).

A subject of the invention is also any in vitro diagnostic or prognostic method for cancers as defined above, in humans or animals, characterized in that it comprises:
  placing a monoclonal antibody as defined above, and more particularly the above-mentioned 35C1 antibody, in the presence of a biological sample taken from an individual, said antibody being if appropriate fixed on a solid support,
  the detection, and if appropriate the quantitation, of the aurora-A protein which may be present in the biological sample using marked reagents, in particular marked antibodies, recognizing either the monoclonal antibody linked to said aurora-A protein, or the aurora-A protein linked to said monoclonal antibody in the complexes formed during the preceding stage between the monoclonal antibody and the protein aurora-A which may be present in the biological sample, this, if necessary, after appropriate rinsing of the solid support.

Advantageously, in the context of the above-mentioned method, the determination of a quantity of aurora-A protein lower than or greater than a physiological threshold determined as a function of the biological sample, shows respectively a good or a poor prognosis for the diagnosed cancer.

A subject of the invention is also a kit for implementing a diagnostic method defined above, characterized in that it comprises:
  a monoclonal antibody as defined above, and more particularly the above-mentioned 35C1 antibody,
  if appropriate, a cell proliferation marker, such as a marker of the PCNA protein, in particular an anti-PCNA antibody.

The invention also relates to the use of a monoclonal antibody as defined above, and more particularly the above-mentioned 35C1 antibody, for the preparation of medicaments intended for the treatment of cancers, such as breast cancers, colorectal cancers and stomach cancers.

Therefore, a subject of the invention is more particularly any pharmaceutical composition, containing a monoclonal antibody as defined above, and more particularly the above-mentioned 35C1 antibody, in combination with a pharmaceutically acceptable vehicle.

A subject of the invention is also the use of a monoclonal antibody as defined above, and more particularly of the above-mentioned 35C1 antibody, for implementing a method for screening inhibitors of aurora-A kinase in which the lowering of the activity of this kinase is measured using said antibody.

A subject of the invention is more particularly any method for screening inhibitors of the aurora-A kinase characterized in that it comprises the following stages:
  the treatment of cells, such as lines derived from different cancers (breast, colon etc.), by the inhibitor tested,
  immunoprecipitation of the aurora-A protein kinase using a monoclonal antibody as defined above, and more particularly the above-mentioned 35C1 antibody, and measurement of the kinase activity, in particular according to the method described in paragraph 3. g) below.

The invention also relates to the method for the preparation of a monoclonal antibody as defined above, and more particularly the above-mentioned 35C1 antibody, characterized in that it comprises the following stages:
  five injections spread over fifteen days to mice of recombinant aurora-A protein kinase produced by E. coli bacteria transformed with a bacterial expression vector in the genome of which the human cDNA coding for aurora-A has been inserted, sacrificing said mice, and fusion between cells of the spleen of these mice and hamster cells immortalized in culture in order to obtain hybridomas,
  screening of the hybridomas producing an antibody capable of immunoprecipitating the recombinant protein used for the immunization of the mice during the preceding stage, and recovery of the positive hybridomas after this first screening,
  screening of the hybridomas recovered in the preceding stage, producing an antibody capable of immunoprecipitating the endogenous aurora-A protein from an extract of human HeLa cells in culture, and recovery of the positive hybridomas after this second screening,
  screening of the hybridomas recovered in the preceding stage, producing an antibody capable of recognizing in indirect immunofluorescence the centrosomes and the poles of the mitotic spindle of human cells in culture, and recovery of the positive hybridomas after this third screening,
  screening of the hybridomas recovered in the preceding stage, producing an antibody capable of immunoprecipitating the endogenous aurora-A protein of mice from an extract of murine cells in culture, and recovery of the positive hybridomas after this fourth screening,
  screening of the hybridomas recovered in the preceding stage, producing an antibody capable of recognizing in indirect immunofluorescence the centrosomes and the poles of the mitotic spindle of murine cells in culture,
  recovery and purification by cloning of a positive hybridoma after the preceding screening stage, and producing a monoclonal antibody possessing all of the properties defined above.

The invention is further illustrated with the detailed description of the 35C1 monoclonal antibody defined above and method for obtaining it.

The human cDNA coding for aurora-A (SEQ ID NO: 1) was inserted into a bacterial expression vector (pET29 Novagene).

The protein kinase was produced in BL21 (DE3)pLysS bacteria and purified by affinity chromatography on an Ni-NTA-agarose column (Qiagen).

The protein purified in the laboratory was then injected into mice (BALB/c).

After five injections spread over 15 days the mice were sacrificed and a fusion was carried out between cells of the spleen of the mouse and hamster cells immortalized in culture in order to obtain hybridomas.

The hybridomas obtained at a quantity of 960 were then tested for their capacity to produce an antibody which recognizes using Western blot the protein used for immunization.

The positive hybridomas after this first screening were then tested using Western blot for their ability to recognize the endogenous aurora-A protein from an extract of human HeLa cells in culture.

The positive hybridomas after this second screening were tested for their ability to recognize in indirect immunofluorescence the centrosomes and the poles of the mitotic spindle of human cells in culture.

The positive hybridomas after this third screening were then tested using Western blot for their ability to recognize the endogenous aurora-A protein of mice from an extract of murine cells in culture.

The positive hybridomas after this fourth screening were tested for their ability to recognize in indirect immunofluorescence the centrosomes and the poles of the mitotic spindle of murine cells in culture.

A hybridoma corresponding to all these criteria was retained and cloned in order to obtain a pure clone. This clone was named 35C1.

It secretes an anti-aurora-A monoclonal antibody which recognizes the human and murine aurora-A kinase.

This anti-aurora-A monoclonal antibody which specifically recognizes the human and murine aurora-A kinase has the following properties:

- it can be used in Western blot (indirect immunodetection of the protein on nitrocellulose or nylon membrane)
- it allows the protein in cells in culture to be located by indirect immnunodetection
- it does not inhibit the enzymatic activity of the kinase in vitro
- it allows the aurora-A kinase from an acellular extract to be purified by immunoprecipitation
- because it does not inhibit the kinase activity of aurora-A it can be used to assay the kinase activity in protein extracts prepared from tissues which present pathologies.

DETAILED DESCRIPTION OF THE INVENTION

Figure 1:
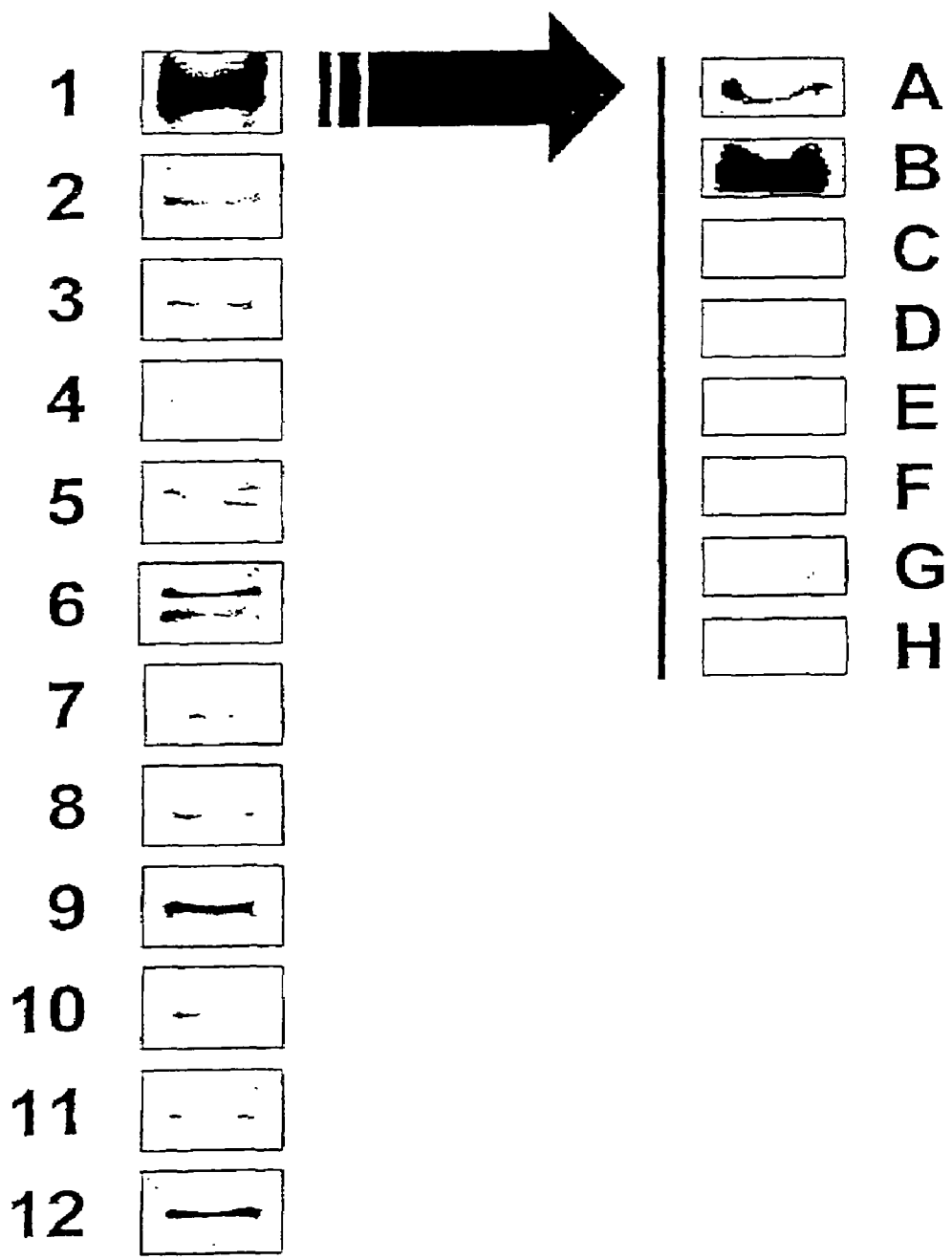
FIG. 1: Scanning of the hybridomas by Western blot. The purified recombinant aurora-A protein was deposited on polyacrylamide-SDS gel and transferred onto a nitrocellulose membrane. The membrane was stained poppy red and the band corresponding to aurora-A was cut out. Each panel corresponds to a piece of membrane with aurora-A. After fusion the cells were distributed in 96-well dishes. In order to screen the presence of anti-aurora-A monoclonals of the aliquots of the supernatants, wells of each colunm are grouped in pools, this being done for each dish. Each pool is then tested using Western blot right-hand colunm from 1 to 12. When a pool is considered to be positive, here the pool number 1, the supernatants of each well which constitute this pool (from A to H) are retested individually. In this specific case the wells A and B contained antibodies, but only well B was retained.
Figure 2:
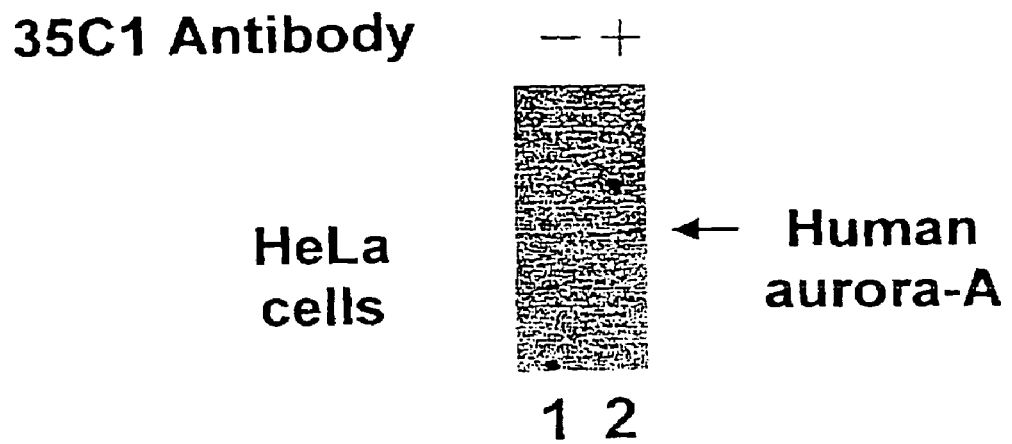
FIG. 2: Western blot. The total acellular extracts are separated on polyacrylamide SDS gel and the gel is transferred onto nitrocellulose membrane. Well 1 does not contain extract and well 2 contains 10 µl of extract (corresponding to $10^6$ cells per ml). The antibody is used at a dilution of 1/100. Only the aurora-A protein of 46 kD is detected.
Figure 2:
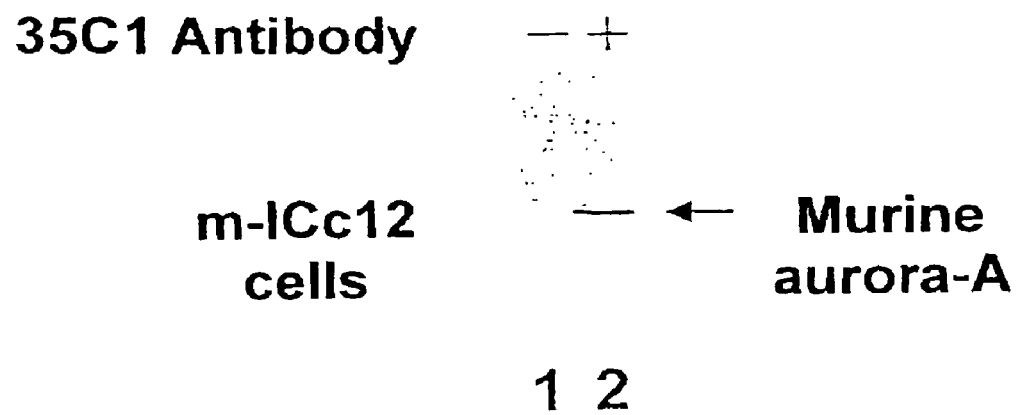

1) Purification of the Recombinant Aurora-A Protein

The cDNA coding for the human aurora-A kinase was cloned in the bacterial expression vector pET29 (supplier Novagen) which allows production of a recombinant protein containing 6 additional histidine residues. The BL21(DE3) pLysS strain of *E. coli* bacterium (supplier Promega) which is deficient in protease and which autolyzes by production of lysozyme after thawing (all these properties facilitate the purification of proteins) was used. The overexpression of the aurora-A(His)6-protein in the bacteria in the growth phase ($OD_{600}$=0.6) is induced at 22° C. by adding 1 mM IPTG (Isopropyl-β-D-thiogalactoside) over 4 hours. The bacteria are then lyzed at 4° C. using in addition to their autolytic property, lysozyme and ultrasonics. The aurora-A-(His)6-protein is then purified by affinity chromatography on a nickel column Ni-NTA-agarose (supplier Qiagen). The protein is eluted with 250 mM imidazole following the Qiagen instructions. The purified protein is then passed over centricon YM-10 (supplier Millipore) in order to place it in a PBS solution (NaCl 136 mM, KCl 26 mM, $Na_2HPO_4$ 2 mM, $KH_2PO_4$ 2 mM, pH 7.2). Fractions of 15 µg of protein were prepared, lyophilized and stored at 4° C.

2) Immunization of the Mouse

A BALB/c mouse was immunized by intraperitoneal route with 15 µg of recombinant aurora-A protein diluted in 50% Freund's complete adjuvant (supplier Sigma). The mouse was then injected with twice 15 μg of recombinant aurora-A protein diluted in 50% Freund's incomplete adjuvant with an interval of three weeks.

When anti-aurora-A antibodies were detected in the blood of the mouse, it was sacrificed and the spleen was removed. Cells in suspension were obtained from this spleen by homogenization with a Dounce.

These spleen cells were fused with SP2/O-Ag14 cells originating from a murine myeloma and obtained from the ECACC (Shulman et al., 1978). A fusion was carried out between $100.10^6$ spleen cells and $20.10^6$ SP2/O-Ag14 cells in 50% polyethylene glycol 1500 (supplier Roche) over 90 minutes at 37° C. The cells were then distributed in 10×96-well dishes containing a HAT selection medium (supplier Sigma Chemicals).

3) Screening of the Hybridomas a) ELISA

100 μl of PBS containing 4 μg/ml of recombinant aurora-A protein were deposited in each well of Elisa plates (96-well plates) and incubated for 36 hours at 4° C. After washing twice with PBS the wells are filled with PBS containing 3% BSA (Bovine Serum Albumin, supplier Sigma) and the plates are incubated overnight at 4° C. The next day 100 μl of each fusion supernatant is transferred into these 96-well plates containing recombinant aurora-A. The plates are incubated at ambient temperature for 2 hours. After washing twice with PBS/BSA, the plates are incubated with an anti-mouse antibody conjugated with phosphatase (Sigma Biochemical). The wells are then washed twice with PBS and once with an AP solution (100 mM Tris pH 9.5, 100 mM NaCl and 5 mM $MgCl_2$). The presence of a monoclonal antibody is detected after filling the wells with 50 μl of AP solution containing the synthetic phosphatase substrate (disodium 4-nitrophenyl phosphate hexahydrate salt) at 5 mg/ml (supplier Merck) and by the appearance of yellow staining in the well.

b) Western Blot Against Recombinant Protein

Ten 96-well plates (8×12) were analyzed by ELISA tests without producing very reproductive results. These plates were then tested by Western blot carried out in the following manner. The recombinant aurora-A protein was subjected to a polyacrylamide-SDS gel electrophoresis and transferred onto nitrocellulose membrane according to the technique described previously (Roghi et al., 1998). The membranes were cut in order to isolate the region corresponding to the locus to where the aurora-A protein migrated. The membrane ends were blocked by incubation in a TBST solution (20 mM Tris-HCl pH 7.5, 150 mM NaCl, 0.05% Tween 20) containing 5% milk for 2 hours at 4° C. Each membrane end was then incubated with the cell supernatants diluted to 1:100 in a TBST solution containing 2.5% milk for 1 hour at 4° C. The immunocomplexes were identified using either a second anti-mouse antibody conjugated with peroxidase or with phosphatase (supplier Sigma Chemicals) at the dilution recommended by the manufacturer. The development of the reaction was carried out by the chemiluminescence technique for the peroxidase (supplier Amersham Pharmacia Biotech) according to the instructions of the supplier or by colorimetry for the phosphatase using the two substrates NBT/BCIP (supplier Sigma Chemicals) according to the manufacturer's instructions.

The wells of each plate were grouped in pools of 8 corresponding to each column of each plate. The presence of monoclonals was analyzed in each pool by Western blot against the recombinant aurora-A protein. Of the 120 pools tested only 19 produced a positive response.

Each of the 8 wells corresponding to each positive pool was tested separately by the same Western blot technique with the aim of identifying which well(s) contain(s) antibodies. FIG. 1 shows an example of results obtained with pool number 2, in this particular case only the wells A and B contained antibodies, the well having been retained.

Of the 120 pools tested only 19 were retained because they produced a very strong positive response. In these 19 pools only 23 wells contained antibodies directed against the recombinant aurora-A protein.

c) Western Blot Against the Endogenous Human Aurora-A Protein

The same Western blot technique was used this time to identify the supernatants capable of recognizing the aurora-A protein from all the proteins of a total acellular extract prepared from human cells in culture.

The cells chosen are HeLa cells. The extracts were prepared from culture dishes containing approximately $10^6$ cells, the cells were lyzed in their dish with 1 ml of a so-called Laemmli solution corresponding to the solution deposited on polyacrylamide-SDS gel (Laemmli 1970), the solution was incubated for 10 minutes at 90° C., sonicated and centrifuged, 10 μl of the supernatant is deposited on the gel.

From the 23 supernatants which had been selected previously only 12 contained an antibody capable of recognizing a protein of 46 kD (expected size for aurora-A) by Western blots carried out on extracts of HeLa cells.

d) Immunofluorescence on Human Cells

An additional stage was introduced into the screening in order to select the antibodies which were capable of decorating the centrosome in human cells in culture. The choice of cells was for the cell line MCF7 which derives from a breast cancer because the aurora-A protein was reported to be overexpressed in these cells.

The technique used is indirect immunofluorescence. The cells are cultured on round glass slips in the 12-well dishes (supplier Coming Inc) for 48 hours. The slips are then washed with a PBS solution and the cells fixed with cold methanol (−20° C.). The cells are then incubated for 30 minutes at ambient temperature in PBS containing 3% BSA. After washing three times with PBS the slips are incubated with the hybridoma supernatants diluted to 1:50 in PBS for 1 hour at ambient temperature. The cells are again washed three times with PBS and incubated at ambient temperature for 1 hour with a second anti-mouse antibody conjugated with fluorescein <<FITC>> (supplier Sigma Chemicals). The slips are washed three times with PBS and the cells are placed between the blade and slip in Mowiol containing antifading agent. The observations were carried out with a Leica DMRXA fluorescence microscope and the images taken with a black and white camera (COHU) were treated with Leica Qfish software.

Of the 12 supernatants retained previously only 4 contained antibodies capable of decorating the centrosomes and the poles of the mitotic spindle of the MCF7 cells. This localization corresponds exactly to that expected for aurora-A kinase.

e) Western Blot Against the Endogenous Murine Aurora-A Protein

With the aim of increasing the selectivity of the screening we tested the 4 supernatants against the orthologous protein of aurora-A in mice. A first screening was carried out by Western blot against acellular extracts of mice cells in culture, m-ICc12 cells. The acellular extracts were prepared as for the human cells and the Western blots were carried out in the same way as previously. Two of the supernatants were capable of recognizing a protein of 46 kD (size also expected for the murine aurora-A kinase).

f) Immunofluorescence on Murine Cells

We verified whether the two supernatants identified previously using Western blot were capable of decorating the centrosomes of cells of mice in culture. We chose the LLC1 cells because they present a very high mitotic index. Only one of the two antibodies was capable of localizing a protein in the centrosomes and at the poles of the mitotic spindle, localizations expected for the aurora-A protein kinase of mice.

g) Assay of the Aurora-A Kinase Activity

Figure 5:
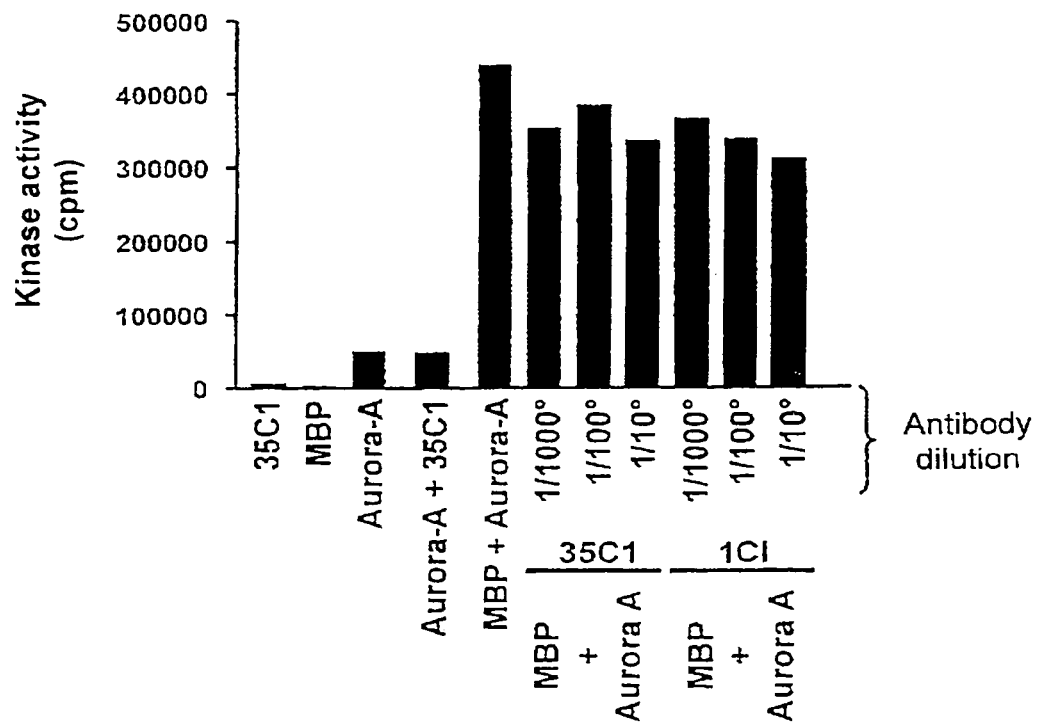
FIG. 5: Activity of the purified human recombinant aurora-A kinase measured in the presence of the 35C1 monoclonal antibody. The 1C1 antibody directed against the aurora-A protein of the xenopus genus and which does not cross with the human protein is used as control. The kinase activity is measured using MBP (Myelin Basic Protein) as substrate.
Figure 6:
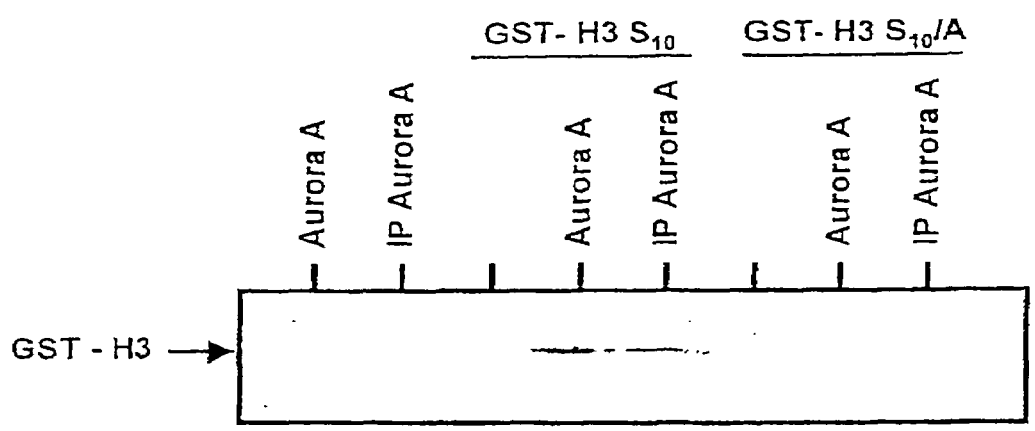
FIG. 6: Activity of the endogenous aurora-A protein immunoprecipitated by the 35 C1 antibody fixed on protein beads A-Dynabeads. The kinase activity is measured on a substrate comprising only one serine which can be phosphorylated. It is a GST construction in fusion with the tail of the H3 histone (with serine 10). A control substrate is also used where the serine 10 is replaced by an alanine. Wells 1, 4 and 7 contain purified recombinant aurora-A are used. Wells 2, 5 and 8 contain immunoprecipitated recombinant aurora-A and are fixed to the antibody and to the A-Sepharose protein. Wells 3 and 6 do not contain kinase. Wells 3, 4 and 5 contain the phosphorylatable substrate GST-H3(S) and wells 6, 7 and 8 the non-phosphorylatable GST-H3(S/A) substrate for the kinases.

Measurements of the aurora-A kinase activity were carried out in 20 µl of Tris-HCl 50 mM pH 7.5, NaCl 50 mM, DTT 1 mM, $MgCl_2$ 10 mM, and ATP 10 µM including 1 µCi of [$\gamma$-$^{32}$P] ATP 3000 Ci/mmole (supplier Amersham Pharmacia Biotech) containing 4 µg myelin basic protein (MBP) for FIG. 5 (supplier Sigma Chemicals) or 10 µl of an extract of bacteria having produced the GST-H3 protein for FIG. 6. The reactions are incubated at 37° C. for 10 minutes. 10 µl of the reaction are analyzed either during counting (FIG. 5) or after migration on polyacrylamide-SDS gel, dried and examined by autoradiography (FIG. 6).

h) Cloning of the Selected Monoclonal

The supernatant that we have selected contained a heterogeneous mixture of cells obtained after fusion. We have subcultured these cells carrying out a limited dilution and obtained 20 clones. The supernatant of these 20 clones was tested using Western blot against the recombinant aurora-A protein, 8 produced a positive response. These 8 supernatants were tested on extracts of human HeLa cells, of murine m-ICc12 cells. Only two supernatants were retained.

These two supernatants were recloned again by limited dilution and retested as previously. The aim of this last cloning was to select a clone which maintained a level of antibody production which can be reproduced after subculture.

Only one of the two clones proved to be stable, it was named 35C1 and retained for storage and production of monoclonal.

i) Properties of the 35C1 Monoclonal (see figures)

The antibody specifically recognizes the human and murine aurora-A protein kinase using Western blot in total acellular extracts (FIG. 1).

Figure 3:
FIG. 3: Indirect immunodetection of aurora-A in human and murine cells. The human cells are MCF7 and the murine cells are LLC 1. In immunofluorescence DNA is detected by staining DAPI (blue), γ-tubulin (red) and aurora-A (green).
Figure 3:
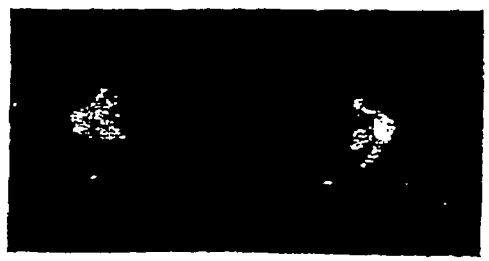

It localizes the aurora-A protein kinase in humans cells and in murine cells in culture (FIG. 3).

Figure 4:
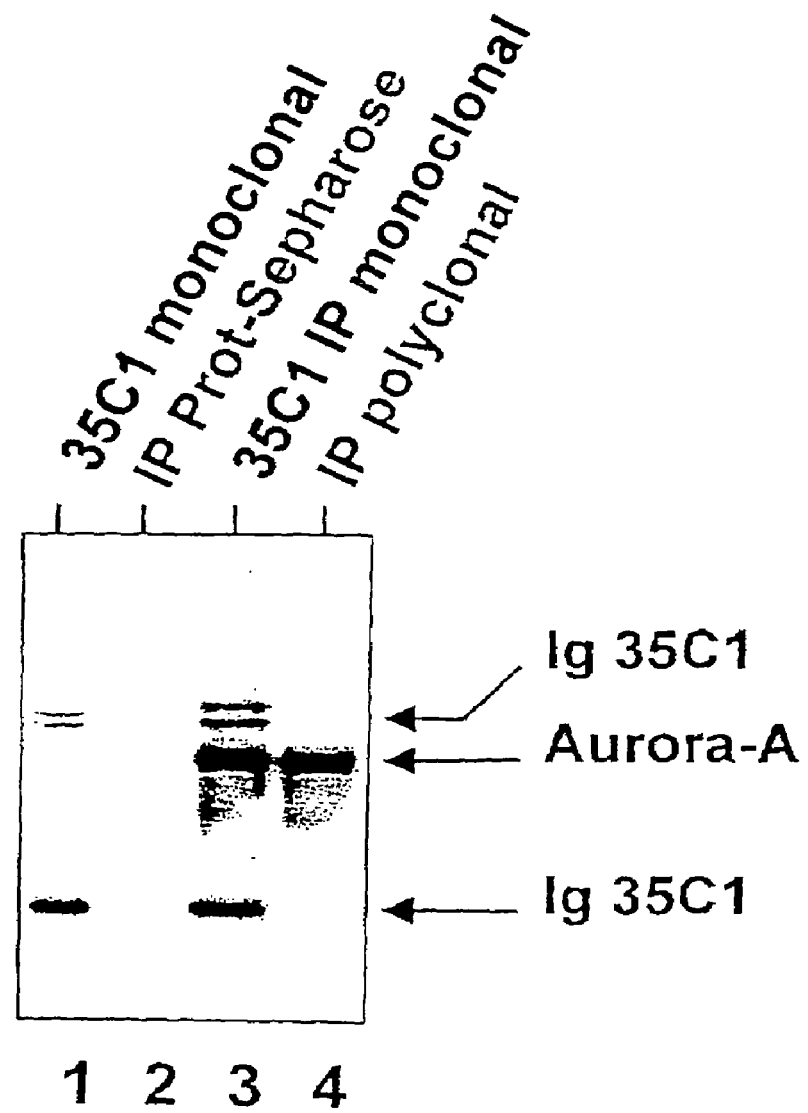
FIG. 4: Immunoprecipitation of aurora-A. The protein is immunoprecipitated by the 35C1 antibody conjugated with the A-Sepharose protein. The immunoprecipitates are separated on a polyacrylamide-SDS gel, the gel is transferred and the immunocomplexes revealed with the 35C1 monoclonal. Well 1: the 35C1 antibody only; well 2: immunoprecipitation carried out with the A-Sepharose protein only; well 3: immunoprecipitation carried out with the 35C1 monoclonal antibody; well 4: immunoprecipitation carried out with an antibody prepared in the laboratory.

It immunoprecipitates the aurora-A protein from extracts of human MCF7 cells (FIG. 4).

It does not inhibit the kinase activity of aurora-A (FIG. 5).

It therefore allows the immunoprecipitation of the aurora-A protein and measurement of its kinase activity while it is still combined with the antibody (FIG. 6) These properties of the 35C1 monoclonal make it a tool of choice for the study of the aurora-A protein kinase.

It can be used in diagnostic and prognostic methods for solid tumours. The level of expression of the mRNA coding for the aurora-A protein is closely correlated with the genetic instability of the breast cancer cells and with a high-grade tumour (Miyoshi et al. 2001). This was very clearly established for breast cancer. On the other hand because of the absence of sufficiently specific monoclonal antibodies, this correlation between the quantity of aurora-A MRNA and the grade of the cancer has not yet been able to be verified at the protein level. The anti-aurora-A 35C1 monoclonal will allow this type of measurements. It allows on the one hand measurement of the quantity of aurora-A protein (Western blot and immunohistochemistry) and on the other hand measurement of the aurora-A activity (immunoprecipitation) in tumours, and thus determination of the threshold of the quantity of aurora-A below which and above which the prognosis for a determined cancer is respectively good or poor.

Moreover, the 35C1 antibody allows testing of the effectiveness of inhibitors of the in vivo aurora-A kinase activity. The aurora-A protein kinase is immunoprecipitated from HeLa cells for example previously treated by the inhibitor and its activity measured in vivo. This allows among other things the evaluation of the stability of the inhibitors in vivo.

Bibliographical References

Bernard M, Sanseau P, Henry C, Couturier A, Prigent C. Cloning of STK13, a third human protein kinase related to *Drosophila* aurora and budding yeast Ipl1 that maps on chromosome 19q13.3-ter. Genomnics. 1998 November 1;53(3): 406-9.

Bischoff J R, Anderson L, Zhu Y, Mossie K, Ng L, Souza B, Schryver B, Flanagan P, Clairvoyant F, Ginther C, Chan C S, Novotny M, Slamon D J, Plowman G D. A homologue of *Drosophila* aurora kinase is oncogenic and amplified in human colorectal cancers. EMBO J 1998 June 1;17(11):3052-65.

Giet R, Prigent C. Aurora/Ipl1p-related kinases, a new oncogenic family of mitotic serine-threonine kinases. J Cell Sci 1999 November;112 (Pt21):3591-601.

Laemmli U. K. Cleavage of structural proteins during the assembly of the head of bacteriophage T4. Nature. 1970 August 15;227(259):680-5.

Miyoshi Y, Iwao K, Egawa C, Noguchi S. Association of centrosomal kinase STK15/BTAK mRNA expression with chromosomal instability in human breast cancers. Int J Cancer 2001 May 1;92(3):370-3.

Prigent C, Gill R, Trower M, Sanseau P. In silico cloning of a new protein kinase, Aik2, related to *Drosophila* Aurora using the new tool: EST Blast. In Silico Biol 1999;1(2):123-8.

Roghi C, Giet R, Uzbekov R., Morin N, Chartrain I, The Guellec R, Couturier A, Doree M, Philippe M, Prigent C. The Xenopus protein kinase pEg2 associates with the centrosome in a cell cycle-dependent manner, binds to the spindle microtubules and is involved in bipolar mitotic spindle assembly. J Cell Sci. 1998 March;111 (Pt5):557-72.

Shulman M, Wilde C D, Kohler G. A better cell line for making hybridomas secreting specific antibodies. Nature 1978 Nov. 16;276(5685):269-70.

Takahashi T, Futamura M, Yoshimi N, Sano J, Katada M, Takagi Y, Kimura M, Yoshioka T, Okano Y, Saji S. (2000) Centrosomal kinases, HsAIRK1 and HsAIRK3, are overexpressed in primary colorectal cancers. *Jpn J Cancer Res* 91(10): 1007-14

Takahashi T, Futamura M, Yoshimi N, Sano J, Katada M, Takagi Y, Kimura M, Yoshioka T, Okano Y, Saji S. Centrosomal kinases, HsAIRK1 and HsAIRK3, are overexpressed in primary colorectal cancers. Jpn J Cancer Res 2000 October; 91(10):1007-14.

Tanaka T, Kimura M, Matsunaga K, Fukada D, Mori H, Okano Y. Centrosomal kinase AIK1 is overexpressed in invasive ductal carcinoma of the breast. Cancer Res 1999 May 1;59(9):2041-4.

Zhou H, Kuang J, Zhong L, Kuo W L, Gray J W, Sahin A, Brinkley B R, Sen S. Tumour amplified kinase STK15/BTAK induces centrosome amplification, aneuploidy and transformation. Nat Genet. 1998 October;20(2):104-6.

The invention claimed is:

1. An isolated 35C1 antibody, wherein said 35C1 antibody specifically recognizes human and murine aurora-A protein kinase and is secreted by the hybridoma deposited at the Collection Nationale de Cultures de Microorganismes (CNCM) of the Institut Pasteur under the number I-3050.

2. The 35C1 antibody of claim 1, wherein said antibody can be fixed on membranes containing human or murine aurora-A protein kinase, allows detection and purification of human and murine aurora-A protein kinase by immunoprecipitation, allows staining of biological tissues where the human or murine aurora-A protein is secreted, and does not inhibit the enzymatic activity of human and murine aurora-A protein kinase; and wherein said 35C1 antibody is obtained by the following steps:
   a) five injections spread over fifteen days to mice of recombinant aurora-A protein kinase, sacrificing said mice, and fusing spleen cells of said mice with hamster cells immortalized in culture in order to obtain hybridomas, wherein said recombinant aurora-A protein kinase is produced by E. coli bacteria transformed with a bacterial expression vector, with human cDNA coding for aurora-A protein kinase having been inserted in the genome of said bacterial expression vector;
   b) screening of said hybridomas producing an antibody capable of irmnunoprecipitating said recombinant aurora-A protein kinase, and recovery of said positive hybridomas after this first screening;
   c) screening of said hybridomas recovered in step b), producing an antibody capable of immunoprecipitating endogenous aurora-A protein kinase from an extract of human HeLa cells in culture, and recovery of said positive hybridomas after this second screening;
   d) screening of said hybridomas recovered in step c), producing an antibody capable of recognizing in indirect immtmofluorescence centrosomes and poles of the mitotic spindle of human cells in culture, and recovery of said positive hybridomas after this third screening;
   e) screening of said hybridomas recovered in step d), producing an antibody capable of immunoprecipitating said endogenous aurora-A protein kinase of mice from an extract of murine cells in culture, and recovery of said positive hybridomas after this fourth screening;
   f) screening of said hybridomas recovered in step e), producing an antibody capable of recognizing in indirect immunofluorescence centrosomes and poles of the mitotic spindle of murine cells in culture; and
   g) recovery and purification by cloning of a positive hybridoma after screening step f), and production of said 35C1 antibody.

3. A cancer diagnostic or prognostic kit comprising said 35C1 antibody of claim 1.

4. The kit of claim 3, further comprising an antibody to a marker of cell proliferation.

5. The kit of claim 4, wherein said marker of cell proliferation is proliferative cell nuclear antigen (PCNA) protein.

6. A phannaceutical composition comprising said 35C1 antibody of claim 1, in combination with a pharmaceutically acceptable vehicle.

7. An in vitro diagnostic or prognostic method for cancers, in a human or an animal, characterized in that it comprises:
   placing the 35C1 antibody of claim 1 in the presence of a biological sample taken from said human or said animal,
   detection of aurora-A protein kinase that may be present in the biological sample using marked reagents recognizing either said 35C1 antibody linked to said aurora-A protein kinase, or the aurora-A protein kinase linked to said 35C1 antibody which may be present in the biological sample.

8. The method of claim 7, characterized in that said 35C1 antibody is fixed on a solid support and the detection is made after rinsing of the solid support.

9. The method of claim 7 or 8, further comprising the quantitation of the aurora-A protein kinase that may be present in said biological sample.

10. The method of claim 7 or 8, characterized in that said cancers are solid tumors selected from the group consisting of breast cancers, stomach cancers, and colorectal cancers.

11. A kit for the implementation of the diagnostic method of claim 7, characterized in that it comprises an isolated 35C1 antibody.

12. The kit of claim 11, is further comprising an anti-PCNA antibody.

* * * * *

SEQUENCE LISTING

<160> NUMBER OF SEQ ID NOS: 2

<210> SEQ ID NO 1
<211> LENGTH: 2253
<212> TYPE: DNA
<213> ORGANISM: Homo sapiens
<220> FEATURE:
<221> NAME/KEY: CDS
<222> LOCATION: (257)...(1468)

<400> SEQUENCE: 1

```
ggaagacttg ggtccttggg tcgcaggtgg gagccgacgg gtgggtagac cgtgggggat    60
atctcagtgg cggacgagga cggcggggac aagggggcggc tggtcggagt ggcggagcgt   120
caagtcccct gtcggttcct ccgtccctga gtgtccttgg cgctgccttg tgcccgccca   180
gcgcctttgc atccgctcct gggcaccgag gcgccctgta ggatactgct tgttacttat   240
tacagctaga ggcatc atg gac cga tct aaa gaa aac tgc att tca gga cct    292
                Met Asp Arg Ser Lys Glu Asn Cys Ile Ser Gly Pro
                 1               5                  10 gtt aag gct aca gct cca gtt gga ggt cca aaa cgt gtt ctc gtg act      340
Val Lys Ala Thr Ala Pro Val Gly Gly Pro Lys Arg Val Leu Val Thr
             15                  20                  25 cag caa att cct tgt cag aat cca tta cct gta aat agt ggc cag gct      388
Gln Gln Ile Pro Cys Gln Asn Pro Leu Pro Val Asn Ser Gly Gln Ala
 30                  35                  40 cag cgg gtc ttg tgt cct tca aat tct tcc cag cgc gtt cct ttg caa      436
Gln Arg Val Leu Cys Pro Ser Asn Ser Ser Gln Arg Val Pro Leu Gln
 45                  50                  55                  60 gca caa aag ctt gtc tcc agt cac aag ccg gtt cag aat cag aag cag      484
Ala Gln Lys Leu Val Ser Ser His Lys Pro Val Gln Asn Gln Lys Gln
             65                  70                  75 aag caa ttg cag gca acc agt gta cct cat cct gtc tcc agg cca ctg      532
Lys Gln Leu Gln Ala Thr Ser Val Pro His Pro Val Ser Arg Pro Leu
         80                  85                  90 aat aac acc caa aag agc aag cag ccc ctg cca tcg gca cct gaa aat      580
Asn Asn Thr Gln Lys Ser Lys Gln Pro Leu Pro Ser Ala Pro Glu Asn
     95                 100                 105 aat cct gag gag gaa ctg gca tca aaa cag aaa aat gaa gaa tca aaa      628
Asn Pro Glu Glu Glu Leu Ala Ser Lys Gln Lys Asn Glu Glu Ser Lys
 110                 115                 120 aag agg cag tgg gct ttg gaa gac ttt gaa att ggt cgc cct ctg ggt      676
Lys Arg Gln Trp Ala Leu Glu Asp Phe Glu Ile Gly Arg Pro Leu Gly
 125                 130                 135                 140 aaa gga aag ttt ggt aat gtt tat ttg gca aga gaa aag caa agc aag      724
Lys Gly Lys Phe Gly Asn Val Tyr Leu Ala Arg Glu Lys Gln Ser Lys
             145                 150                 155 ttt att ctg gct ctt aaa gtg tta ttt aaa gct cag ctg gag aaa gcc      772
Phe Ile Leu Ala Leu Lys Val Leu Phe Lys Ala Gln Leu Glu Lys Ala
         160                 165                 170 gga gtg gag cat cag ctc aga aga gaa gta gaa ata cag tcc cac ctt      820
Gly Val Glu His Gln Leu Arg Arg Glu Val Glu Ile Gln Ser His Leu
     175                 180                 185 cgg cat cct aat att ctt aga ctg tat ggt tat ttc cat gat gct acc      868
Arg His Pro Asn Ile Leu Arg Leu Tyr Gly Tyr Phe His Asp Ala Thr
 190                 195                 200 aga gtc tac cta att ctg gaa tat gca cca ctt gga aca gtt tat aga      916
Arg Val Tyr Leu Ile Leu Glu Tyr Ala Pro Leu Gly Thr Val Tyr Arg
 205                 210                 215                 220
```

-continued

| | |
|---|---|
| gaa ctt cag aaa ctt tca aag ttt gat gag cag aga act gct act tat<br>Glu Leu Gln Lys Leu Ser Lys Phe Asp Glu Gln Arg Thr Ala Thr Tyr<br>225 230 235 | 964 |
| ata aca gaa ttg gca aat gcc ctg tct tac tgt cat tcg aag aga gtt<br>Ile Thr Glu Leu Ala Asn Ala Leu Ser Tyr Cys His Ser Lys Arg Val<br>240 245 250 | 1012 |
| att cat aga gac att aag cca gag aac tta ctt ctt gga tca gct gga<br>Ile His Arg Asp Ile Lys Pro Glu Asn Leu Leu Leu Gly Ser Ala Gly<br>255 260 265 | 1060 |
| gag ctt aaa att gca gat ttt ggg tgg tca gta cat gct cca tct tcc<br>Glu Leu Lys Ile Ala Asp Phe Gly Trp Ser Val His Ala Pro Ser Ser<br>270 275 280 | 1108 |
| agg agg acc act ctc tgt ggc acc ctg gac tac ctg ccc cct gaa atg<br>Arg Arg Thr Thr Leu Cys Gly Thr Leu Asp Tyr Leu Pro Pro Glu Met<br>285 290 295 300 | 1156 |
| att gaa ggt cgg atg cat gat gag aag gtg gat ctc tgg agc ctt gga<br>Ile Glu Gly Arg Met His Asp Glu Lys Val Asp Leu Trp Ser Leu Gly<br>305 310 315 | 1204 |
| gtt ctt tgc tat gaa ttt tta gtt ggg aag cct cct ttt gag gca aac<br>Val Leu Cys Tyr Glu Phe Leu Val Gly Lys Pro Pro Phe Glu Ala Asn<br>320 325 330 | 1252 |
| aca tac caa gag acc tac aaa aga ata tca cgg gtt gaa ttc aca ttc<br>Thr Tyr Gln Glu Thr Tyr Lys Arg Ile Ser Arg Val Glu Phe Thr Phe<br>335 340 345 | 1300 |
| cct gac ttt gta aca gag gga gcc agg gac ctc att tca aga ctg ttg<br>Pro Asp Phe Val Thr Glu Gly Ala Arg Asp Leu Ile Ser Arg Leu Leu<br>350 355 360 | 1348 |
| aag cat aat ccc agc cag agg cca atg ctc aga gaa gta ctt gaa cac<br>Lys His Asn Pro Ser Gln Arg Pro Met Leu Arg Glu Val Leu Glu His<br>365 370 375 380 | 1396 |
| ccc tgg atc aca gca aat tca tca aaa cca tca aat tgc caa aac aaa<br>Pro Trp Ile Thr Ala Asn Ser Ser Lys Pro Ser Asn Cys Gln Asn Lys<br>385 390 395 | 1444 |
| gaa tca gct agc aaa cag tct tag gaatcgtgca gggggagaaa tccttgagcc<br>Glu Ser Ala Ser Lys Gln Ser *<br>400 | 1498 |
| agggctgcca tataacctga caggaacatg ctactgaagt ttatttttacc attgactgct | 1558 |
| gccctcaatc tagaacgcta cacaagaaat atttgtttta ctcagcaggt gtgccttaac | 1618 |
| ctccctattc agaaagctcc acatcaataa acatgacact ctgaagtgaa agtagccacg | 1678 |
| agaattgtgc tacttatact ggttcataat ctggaggcaa ggttcgactg cagccgcccc | 1738 |
| gtcagcctgt gctaggcatg gtgtcttcac aggaggcaaa tccagagcct ggctgtgggg | 1798 |
| aaagtgacca ctctgccctg accccgatca gttaaggagc tgtgcaataa ccttcctagt | 1858 |
| acctgagtga gtgtgtaact tattggggttg gcgaagcctg gtaaagctgt tggaatgagt | 1918 |
| atgtgattct ttttaagtat gaaaataaag atatatgtac agacttgtat tttttctctg | 1978 |
| gtggcattcc tttaggaatg ctgtgtgtct gtccggcacc ccgtaggcc tgattgggtt | 2038 |
| tctagtcctc cttaaccact tatctcccat atgagagtgt gaaaaatagg aacacgtgct | 2098 |
| ctacctccat ttagggattt gcttgggata cagaagaggc catgtgtctc agagctgtta | 2158 |
| agggcttatt ttttaaaac attggagtca tagcatgtgt gtaaacttta aatatgcaaa | 2218 |
| taaataagta tctatgtcta aaaaaaaaaa aaaaa | 2253 |

<210> SEQ ID NO 2
<211> LENGTH: 403
<212> TYPE: PRT
<213> ORGANISM: Homo sapiens

```
<400> SEQUENCE: 2

Met Asp Arg Ser Lys Glu Asn Cys Ile Ser Gly Pro Val Lys Ala Thr
  1               5                  10                  15

Ala Pro Val Gly Gly Pro Lys Arg Val Leu Val Thr Gln Gln Ile Pro
             20                  25                  30

Cys Gln Asn Pro Leu Pro Val Asn Ser Gly Gln Ala Gln Arg Val Leu
         35                  40                  45

Cys Pro Ser Asn Ser Ser Gln Arg Val Pro Leu Gln Ala Gln Lys Leu
     50                  55                  60

Val Ser Ser His Lys Pro Val Gln Asn Gln Lys Gln Lys Gln Leu Gln
 65                  70                  75                  80

Ala Thr Ser Val Pro His Pro Val Ser Arg Pro Leu Asn Asn Thr Gln
                 85                  90                  95

Lys Ser Lys Gln Pro Leu Pro Ser Ala Pro Glu Asn Asn Pro Glu Glu
             100                 105                 110

Glu Leu Ala Ser Lys Gln Lys Asn Glu Glu Ser Lys Lys Arg Gln Trp
         115                 120                 125

Ala Leu Glu Asp Phe Glu Ile Gly Arg Pro Leu Gly Lys Gly Lys Phe
    130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
        195                 200                 205

Ile Leu Glu Tyr Ala Pro Leu Gly Thr Val Tyr Arg Glu Leu Gln Lys
    210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
            260                 265                 270

Ala Asp Phe Gly Trp Ser Val His Ala Pro Ser Ser Arg Arg Thr Thr
        275                 280                 285

Leu Cys Gly Thr Leu Asp Tyr Leu Pro Pro Glu Met Ile Glu Gly Arg
    290                 295                 300

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335

Thr Tyr Lys Arg Ile Ser Arg Val Glu Phe Thr Phe Pro Asp Phe Val
            340                 345                 350

Thr Glu Gly Ala Arg Asp Leu Ile Ser Arg Leu Leu Lys His Asn Pro
        355                 360                 365
```

-continued

```
Ser Gln Arg Pro Met Leu Arg Glu Val Leu Glu His Pro Trp Ile Thr
    370                 375                 380

Ala Asn Ser Ser Lys Pro Ser Asn Cys Gln Asn Lys Glu Ser Ala Ser
385                 390                 395                 400

Lys Gln Ser
```